United States Patent
Brooks et al.

(10) Patent No.: US 6,558,694 B2
(45) Date of Patent: May 6, 2003

(54) ZINC CHLORIDE UNIT DOSE PACKAGING, APPLICATOR, AND METHOD OF USE IN TREATING CANCER AND OTHER SKIN DISEASES

(76) Inventors: Norman A. Brooks, 16420 Marbro Dr., Encino, CA (US) 91436; Leslee S. Brooks, 16420 Marbro Dr., Encino, CA (US) 91436

( * ) Notice: Subject to any disclaimer, the term of this patent is extended or adjusted under 35 U.S.C. 154(b) by 91 days.

(21) Appl. No.: 09/505,618

(22) Filed: Feb. 16, 2000

(65) Prior Publication Data

US 2002/0081328 A1 Jun. 27, 2002

Related U.S. Application Data

(60) Provisional application No. 60/120,656, filed on Feb. 19, 1999.

(51) Int. Cl.[7] ............... A61K 13/00; A61K 9/14; A61K 31/74
(52) U.S. Cl. ............ 424/449; 424/443; 424/484; 424/485; 424/486; 424/487; 424/488; 424/78.03; 424/448
(58) Field of Search ............... 424/443, 449, 424/448, 145, 195.1

(56) References Cited

U.S. PATENT DOCUMENTS

| | | | | |
|---|---|---|---|---|
| 2,344,830 A | * | 3/1944 | Mohs et al. ................. | 167/63 |
| 4,224,339 A | * | 9/1980 | Van Scott et al. ......... | 424/289 |
| 4,229,437 A | * | 10/1980 | Likens, deceased et al. ................. | 424/145 |
| 4,335,110 A | | 6/1982 | Collins | |
| 4,515,779 A | * | 5/1985 | Elliott ....................... | 424/145 |

(List continued on next page.)

OTHER PUBLICATIONS

Norman A. Brooks, MD, "Mohs Surgery Fixed–Tissue Tichnique", p. 267–274, Aug. 1998.*

Norman A. Brooks, MD, "Fixed–Tissue Micrographic Surgery".

(List continued on next page.)

Primary Examiner—Thurman K. Page
Assistant Examiner—Isis Ghali
(74) Attorney, Agent, or Firm—Kelly Bauersfeld Lowry & Kelley, LLP

(57) ABSTRACT

An improved method for the treatment of melanoma and skin diseases which utilizes a zinc chloride fixative mixture is provided. The active ingredients of the fixative mixture include zinc chloride (a deeply penetrating, tissue killing histologic preservative), and the anti-cancer plant alkaloids sanguinarine and chelerythrine. Zinc chloride allows the surgeon to perform a complete conventional surgical excision around and below a melanomatous tumor through painless, bloodless dead tissue, and because the microscopic structures are fixed in place by the zinc chloride, the excised tissue can be examined by a pathologist to confirm complete excision and clearance of the melanoma. Although zinc chloride fixative paste has been shown to be an effective treatment for human skin cancer and melanoma, this treatment has been overlooked by the medical community. The paste is difficult to maintain and complicated to apply to the affected skin. This invention allows the active ingredients of zinc chloride fixative paste to be effectively administered to the skin by providing single-use dose specific storage, application, dressing, and administration systems needed to facilitate the use of topical zinc chloride mixtures and/or zinc chloride pastes in the treatment of melanoma and other skin diseases. Enhanced zinc chloride mixture formulations are described.

21 Claims, 9 Drawing Sheets

U.S. PATENT DOCUMENTS

| | | | | |
|---|---|---|---|---|
| 4,588,590 A | * | 5/1986 | Bernstein | 424/195.1 |
| 4,599,228 A | * | 7/1986 | Ladanyi | 424/52 |
| 4,774,229 A | * | 9/1988 | Jordan | 514/25 |
| 4,895,727 A | * | 1/1990 | Allen | 424/642 |
| 4,917,895 A | * | 4/1990 | Lee et al. | |
| 5,395,610 A | * | 3/1995 | King | 424/10 |
| 5,559,235 A | * | 9/1996 | Luzzio et al. | 544/361 |
| 6,124,311 A | * | 9/2000 | Chandrasekhar et al. | |

OTHER PUBLICATIONS

Richard S. Kalish, MD, PhD. et al., "Experimental Rationale for Treatment of High Risk Human Melanoma with Zinc Chloride Fixative Paste".

Norman A. Brooks, MD, "Mohs Surgery Fixed–Tissue Technique".

* cited by examiner

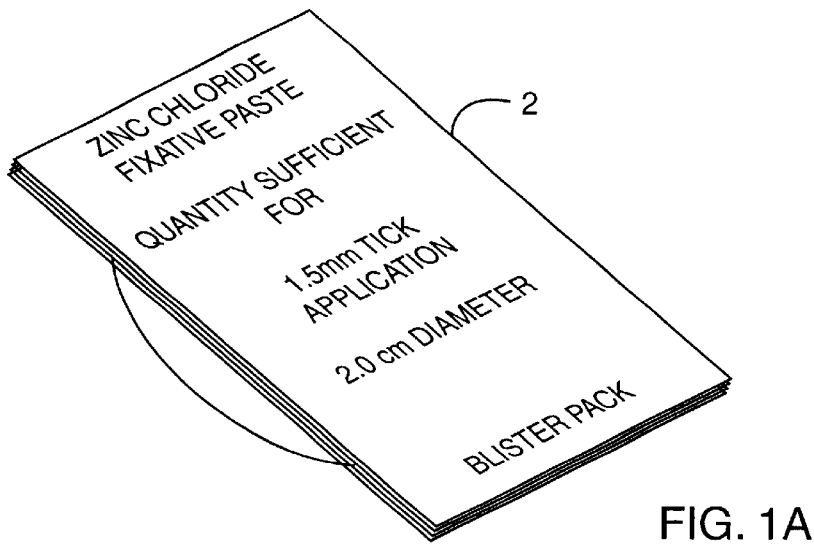
FIG. 1A
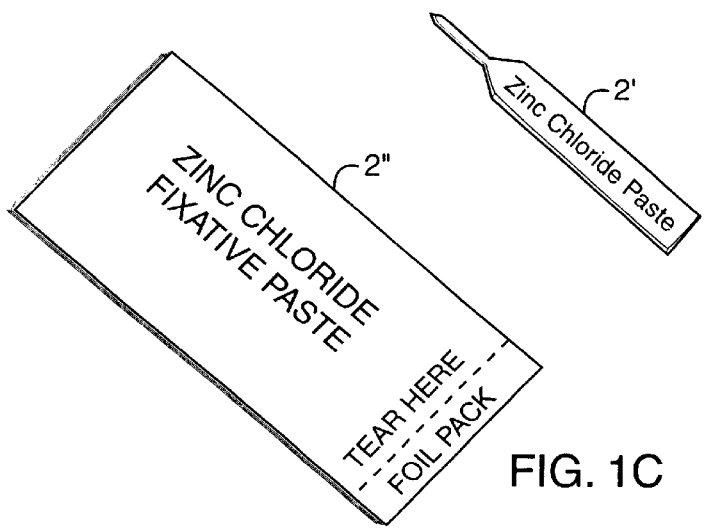
FIG. 1B
FIG. 1C
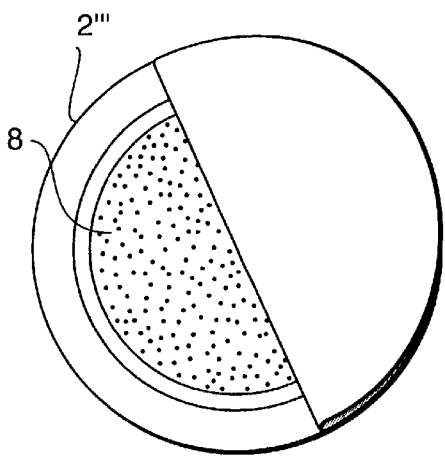
FIG. 1D

ZINC CHLORIDE UNIT DOSE PACKAGING, APPLICATOR, AND METHOD OF USE IN TREATING CANCER AND OTHER SKIN DISEASES

RELATED APPLICATION

This application claims priority from provisional application Ser. No. 60/120,656 filed Feb. 19, 1999.

BACKGROUND OF THE INVENTION

The present invention relates to the treatment of human melanoma, basal and squamous cell skin cancer, and a variety of other skin tumors and skin diseases. More particularly, the present invention relates to unit dose packaging of a zinc chloride mixture and used in a dosage specific applicator for the treatment of these skin diseases.

Melanoma is a potentially fatal form of skin cancer, usually appearing as a black or dark brown mole. The conventional treatment of cutaneous melanoma has been excision with a deep and wide margin of normal appearing tissue surrounding the tumor depending on the depth and thickness of the cancerous mole. However, microscopic satellite sites potentially occurring in the otherwise normal appearing skin surrounding the melanoma may be disturbed, and host resistance may be reduced following the excision of the melanoma. A decrease in host resistance may result in the appearance of cancer in distant sites of the body (metastases). (Smolle, J. et al, *Does Surgical Removal of Primary Melanoma Trigger Growth of Occult Metastases? An Analytical Epidemiological Approach.* Dermatologic Surgery, November, 1997). Cancer metastases can cause death of the patient. Although it is common to excise a margin of tissue surrounding the tumor, it is well known that increasing the size of the surgical margin to greater and greater extent does not affect survival rate.

Adjuvant therapy has been recommended for melanoma patients in whom clinical and histopathological parameters indicate a high risk of relapse. Interferon alpha 2B has been approved by the United States Food and Drug Administration for treatment of such high-risk melanomas. However, the survival from high-risk melanomas remains poor, and additional modalities are needed. Clinical evidence shows that the pre-surgical application of zinc chloride paste improves the prognosis of melanoma.

Zinc chloride was discovered by Sir Humphry Davy of Bristol, United Kingdom, in 1815. It was used for the treatment of cancer by Canquoin of Paris and by Bougard of Brussels in the early part of the nineteenth century. Zinc chloride is a very potent chemical which deeply penetrates and kills tissue.

While a research assistant in the department of zoology at the University of Wisconsin, Dr. Frederic E. Mohs, founder of the American College of Mohs Micrographic Surgery and Cutaneous Oncology, observed that the injection of zinc chloride into cancerous tissue not only caused tissue necrosis (cell death), but, additionally, the microscopic structure of the killed tissue was retained as if the tissue had been excised and immersed in a fixative, or histologically preserving solution. Dr. Mohs developed an anti-skin cancer paste containing zinc chloride and the escharotic bloodroot plant, *Sanguinaria canadensis*. The formula is as follows: Stibnite (alpha, beta-Diphenylethylene 80-mesh sieve), 40 g; *Sanguinaria canadensis*, 10 g; and zinc chloride, saturated solution, 34.5 mL (zinc chloride 45% by weight).

Since 1941, Dr. Mohs has published a textbook and numerous articles on the successful treatment of skin cancer and melanoma using this zinc chloride paste. Dr. Mohs referred to the paste as "zinc chloride fixative paste" and the surgery as "chemosurgery" or "fixed-tissue micrographic surgery". For the treatment of melanoma, Mohs utilized a layer by layer excision technique in addition to in situ fixation of the tumorous tissue with zinc chloride fixative paste. In fixed-tissue surgery, a clinically apparent melanoma is first treated with zinc chloride fixative paste prior to any biopsy or debulking procedure. The next day, a layer of fixed tissue is excised and frozen histologic sections are made for microscopic examination to confirm the clinical diagnosis of melanoma. The melanoma is then excised layer-by-layer, with each successive layer first fixed in situ, then conservatively removed for microscopic scanning of the entire undersurface utilizing frozen histologic sections cut horizontally from the bottom of the excised specimens. The edges of the specimens are color coded by the application of dyes for precise orientation as the sections are scanned under the microscope. The zinc chloride paste is reapplied as necessary until a melanoma-free plane has been reached. An extra margin of surrounding tissue is then removed by zinc chloride fixed-tissue surgery to encompass satellite deposits that may be present in the surrounding skin lymphatics.

In 1977, Mohs published data on 103 consecutive patients with mainly advanced melanomas treated with zinc chloride fixative paste (64% Clark's level V lesions, 20% regional lymph node involvement). The 5-year cure rate was compared with a series of melanomas treated conventionally by surgical excision alone at the Massachusetts General Hospital, and stratified by Clark's level of invasion. In the Clark's melanoma classification system there are five levels. Clark's I being the most superficial and V being the deepest invasion of the skin and penetration into fatty tissue under the skin. Both studies were completed in 1968. In the conventional surgery series, all the melanomas were primary tumors without regional lymph node metastases, and the incidence of level V invasion was only one-sixth that of the zinc chloride fixative cases. Despite a 20% incidence of nodal metastases and a six times greater incidence of level V melanomas in the fixed tissue series, a significant ($p=0.003$) one and a half times improvement in five year survival was achieved using zinc chloride fixative paste. (Mohs, FE: *Chemosurgery for melanoma.* Arch Dermatol 133: 285–291,1977; Brooks, N A: *Fixed-tissue micrographic surgery in the treatment of cutaneous melanoma,* J. Dermatol Surg. Oncol. 1992; 18: 999–1000.)

Similar results have been found with the common skin cancers, basal cell and squamous cell carcinoma. In 1986, Dr. Almeida Goncalves and Dr. Ricardo Azevedo published their experience using a zinc chloride paste with a group of patients which consisted of 179 basal cell carcinomas and 33 squamous cell carcinomas of varying diameters. All patients had more than five years follow-up and no tumor persistence or recurrence was observed. (Goncalves J C A, *Chemosurgery without systematized microscopic control for malignant skin tumors—A new simplified technique.* Skin Cancer, 1986; 1: 137–150). This study continued until 400 basal cell and squamous cell skin cancers had been treated. Only one persistence had occurred resulting in a cure rate of 99.7%, which is much higher than the reported cure rate for curettage and desiccation, the most commonly used method for the treatment of basal and squamous cell skin cancer (Goncalves, J C A and Azevedo, R B R. *An attempt at reducing pain in cancer patients treated by chemosurgery without systemized microscopic control.* Skin Cancer, 1998; 13: 145–161.Salasche, S J. *Status of curettage and desicca-* tion in the treatment of primary basal cell carcinoma. J American Acad of Dermatology, 1984; vol 10: 285–287).

While the use of zinc chloride chemosurgery has been shown to produce remarkable life-saving results, these treatments have not been grasped by the medical community. This has been due, in part, to the lack of understanding of the manner in which zinc chloride prevents relapse in cancer and increases survival rates, the difficulty in following the Mohs procedure, and the potency and instability of zinc chloride pastes. A detailed discussion of why these treatments have been overlooked and underestimated follows.

The Mohs Technique is Difficult to Perform

The Mohs method is a laborious and time consuming process, requiring the repetitive examination of multiple layers of zinc chloride fixed tissue. Furthermore, Mohs taught of the use of dressings which are complicated and difficult to apply for the application of zinc chloride paste to the skin. In the Mohs' dressing technique, first a layer of dry cotton is applied over the zinc chloride paste to help hold it in place on the skin, then a gauze-backed, petrolatum spread cotton dressing is overlapped to make an air-tight closure. This in turn is fastened securely with Micropore paper tape. (Mohs F E, *Mohs Chemosurgery Microscopically Controlled Surgery for Skin Cancer.* Charles C. Thomas 1978; p 14) The Mohs' dressing is messy and difficult to apply. Unless properly applied, the zinc chloride paste can leak out beyond the limits of the intended application.

The Rationale for using Zinc Chloride Paste has been Poorly Understood

Attempts have been made to simplify the original fixed-tissue technique based on a misunderstanding of how zinc chloride paste works in the cure of melanoma. A method known as the hybrid fixed-tissue technique was investigated. It involves excising melanomas by fresh tissue surgery and then treating the wound base with zinc chloride fixative paste in order to kill tissue and reduce the likelihood of disturbing microsatellites. In the hybrid fixed-tissue technique, the melanoma is excised without any fixation of the tumor. A melanoma tumor registry maintained by Dr. Stephen Snow, at the University of Wisconsin, Madison, compared 113 cases treated with the hybrid fixed-tissue technique (fresh tissue excision followed by fixative paste to the wound) with 61 cases treated by Mohs' fresh tissue technique without zinc chloride. No difference in five year survival for thin and intermediate thickness melanoma was determined, putting in question the efficacy of the hybrid method. (Snow, S N, et al: *Cutaneous malignant melanoma treated by Mohs surgery.* Dermatol Surg. 23: 1055–1060, 1997).

The inventor initiated and helped direct a murine melanoma experiment in which a key vaccine-like property of zinc chloride paste was discovered. (Brooks, Kalish, Siegal, et al., *Experimental rationale for treatment of high-risk human melanoma with zinc chloride fixative paste.* Dermatologic Surgery, September, 1998, Vol 24: 1021–1025). In the experiment two murine melanoma lines were used: (1) the immunogenic K1735p melanoma and (2) the poorly immunogenic B16-F1 melanoma as a control. Mice were injected intradermally with melanoma cells, and the subsequent tumors were treated either by excision or zinc chloride paste followed by excision. After a one week rest, the mice were challenged at a different site with a second injection of the same melanoma cell line, and tumor appearance at the second site was monitored. Mice with K1735p melanoma treated with zinc chloride paste had a significant reduction in tumor development at the second challenge site relative to excision alone. Similar treatment of the poorly immunogenic B16-F1 melanoma did not result in resistance to tumor challenge relative to excision alone.

It was concluded that the zinc chloride paste acted as an immune adjuvant, inducing specific host cell mediated resistance to the immunogenic K1735p melanoma. Based upon a comparison of these results with the hybrid technique test results obtained by Dr. Snow, the survival benefit of zinc chloride fixation is related to not only the actual killing of the cells by the zinc chloride paste, but also to an immunologic adjuvant effect requiring the presence of melanoma cells and fixation of the tumor. By removing the tumor first, Dr. Snow did not get the immunologic reaction necessary to establish a melanoma immunity. Although only tested with melanoma, it is believed that similar immunologic effects are obtained with other forms of skin cancer and abnormal skin growths.

Zinc Chloride Pastes are not Stable

Zinc chloride is highly deliquescent and following manufacture the paste can become excessively liquefied in humid conditions or dry to a hardened mass during dry conditions, making the preparation ineffective. When zinc chloride is stored in a large jar in hot, humid weather the paste can draw in excess moisture and become too watery and runny to be useful. The jar of fixative often must be kept in a calcium chloride desiccator during the moist summer months. Conversely, dry atmosphere produced by heating in winter can cause the paste to dry and harden into an ineffective mass. (Mohs F E, *Mohs Chemosurgery Microscopically Controlled Surgery for Skin Cancer.* Charles C. Thomas 1978; p.13) Modern medical practitioners are often unwilling to spend the time required to stabilize the paste before using.

The Vast Majority of Modern Medical Practitioners are Unaware of the Proper Dosage of Zinc Chloride Paste Required in the Treatment of Melanoma, Skin Cancer and other Skin Diseases.

Zinc chloride is an extremely potent and deeply penetrating agent. The proper dose varies widely depending on the size, depth of invasion, type and location of the tumor. An improper dosage can result in a deep ulcerated wound requiring months to heal. Precise dose is necessary yet zinc chloride paste has never been available in specific dosed packages.

Accordingly, what is needed is a technique which effectively simplifies the Mohs original technique. What is also needed is an improved method of applying, administering, storing and dosing zinc chloride mixtures and/or zinc chloride pastes in the treatment of melanoma and other skin diseases. The present invention fulfills these needs and provides other related advantages.

SUMMARY OF THE INVENTION

The present invention resides in a medicinal zinc chloride mixture used in treating skin diseases, unit dose packaging, an applicator for the zinc chloride mixture, and a method of using the zinc chloride mixture to treat cancer and other skin diseases.

The zinc chloride mixture generally comprises zinc chloride, a granular matrix and *sanguinaria canadensis*. The preferred mixture comprises, in a saturated zinc chloride 34.5 mL solution, 45% concentration zinc chloride by weight, 40 grams of stibnite, 10 grams of *sanguinaria canadensis*.

In treating a skin tumor the first step is to visually examine the abnormal skin growth. If cancer is suspected, a biopsy may be performed to determine with certainty that the abnormal growth is in fact cancerous. A skin penetration enhancing agent such as a keratolytic acid is then placed on the lesion followed by the zinc chloride mixture. Eighteen to twenty-four hours is allowed for the complete penetration of the zinc chloride. The site is subsequently inspected to determine clearance of the abnormal skin growth. If the lesion is cured, no further treatment is undertaken. If not, the process is repeated until the lesion is cured. The wound is allowed to heal spontaneously by second intention. The inspection step may include performing a biopsy to determine the clearance of a cancerous growth.

When treating plantar warts, after examining and diagnosing the lesions, the individual warts are pared with a surgical blade to remove an outer dead keratin layer. Keratolytic acid and then zinc chloride are applied to the wart. The site is later observed for healing and the process is repeated after approximately three weeks if the wart is not cured. If the lesion is cured, there is no further treatment.

In treating basal and squamous cell carcinomas, the lesion site is first visually observed, a clinical diagnosis made, and photographs may be taken. A fresh tissue biopsy of the suspected cancer may be performed, and if the lesion is benign, there is no further treatment. If the lesion is determined to be malignant, a keratolytic acid, such as trichloracetic acid, followed by the zinc chloride mixture is applied to the judged area of malignant involvement. Since zinc chloride paste preserves histology a tumor fragment may be biopsied without bleeding or pain approximately 24 hours after the application of zinc chloride.

Over time, the treated area of basal and squamous cell carcinoma becomes gray and necrotic with surrounding inflammation. After one to two weeks, the tumor sloughs off spontaneously or is easily removed with a forceps. The resulting ulcer is examined for a clean, smooth surface and normal appearing edges without evidence of residual tumor. If the tumor persists, the process is repeated until the tumor is eliminated. The wound is then allowed to heal by second intention. The skin cancer site is observed intermittently over a five year period for any evidence of local recurrence.

Treatment of melanomas also involves visually examining and diagnosing the skin site, as well as the possibility of taking photographs. A fresh tissue biopsy is taken from the thickest part of the tumor utilizing a 3.5 mm to 4.0 mm punch biopsy instrument. If the lesion is found to be benign, no further treatment is given. However, if the biopsy confirms melanoma, a keratolytic acid, such as trichloracetic acid, followed by the zinc chloride mixture is applied to the remaining melanomatous tumor and surrounding margin of normal appearing skin. The margin may vary from 6 mm to 1.5 cm depending on the size and thickness of the tumor.

The following day, a conventional surgical excision is performed on the tumor with a deep and wide margin of previously killed surrounding tissue. The excision is performed within 1 mm to 2 mm of the outer edge of the zinc chloride fixed tissue. Zinc chloride is applied to the excisional surface immediately following surgery. The 1 mm to 2 mm thin necrotic wall remains in place to provoke a surrounding inflammation.

Conventional microscopic examination of the excised tissue using traditional permanent histologic sections cut perpendicular to the skin in the vertical plane is conducted. Dyes may be applied to the edges of the excised tissue for precise tumor orientation. The tissue is examined microscopically to determine clearance of the melanomatous tumor to the deep and side margins. If the side or deep margins show inadequate microscopic tumoral clearance, the application of the zinc chloride mixture is repeated until adequate margins are achieved. After one to two weeks, the necrotic thin wall tissue remaining in the ulcer sloughs off or is easily removed with forceps. The wound heals spontaneously by second intention.

The zinc chloride unit dose packaged mixture is stored in a humectantly sealed container which maintains the stability of the paste. A dose specific single use quantity of zinc chloride mixture may be applied to the skin from the container. The mixture may be held in place with a transdermal applicator or alternately, the mixture may be in a humectantly sealed, multi-layered, flexible transdermal applicator which is positioned directly on the skin growth site. The applicator allows specific dosing and maintains the physical properties of the mixture.

The transdermal applicator may contain special pharmacologically active additives and/or skin penetration chemical enhancers (e.g. keratolytic agents and/or acids), mixed with zinc chloride mixture. Alternatively, the special additives may be contained in the applicator without zinc chloride. Transdermal applicators containing special pharmacologically active ingredients without zinc chloride may be utilized to enhance a previously applied zinc chloride mixture and hold it in place on the skin. For purposes of simplicity the contents of the transdermal applicators will be hereinafter referred to as the "zinc chloride mixture".

The applicator is generally comprised of a fluid impermeable backing and the zinc chloride mixture adjoining the backing. Preferably, the applicator includes an adhesive substrate disposed on the backing so that the applicator can be adhered to the skin site.

In its most simple form, the applicator includes an adhesive substrate impregnated with the zinc chloride mixture layered between the backing and a liquid impermeable peel away strip temporarily positioned along one side of the backing.

In a more complex form, the applicator includes the fluid impermeable backing, an adhesive substrate disposed on the backing so that the applicator can be adhered to the skin site, and a secondary backing substrate flexibly affixed to the backing to form a reservoir for the zinc chloride mixture between the secondary backing and the peel away strip. The secondary backing typically includes a flange intended to prevent the zinc chloride mixture from seeping out from the intended skin site.

In another form, the transdermal applicator includes the fluid impermeable backing, an adhesive substrate disposed on the backing so that the applicator can be adhered to the skin site, and a polymer drug matrix impregnated with the zinc chloride mixture disposed between the backing and the peel away strip.

In yet another form, the transdermal applicator includes the fluid impermeable backing, an adhesive substrate disposed on the backing so that the applicator can be adhered to the skin site, and a rate controlling membrane disposed between the zinc chloride mixture and the peel away strip to control the rate at which the zinc chloride is administered.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIGS. 1A–1D show four zinc chloride unit dosed packages, wherein

FIG. 1A is a blister pack containing a specific dose of zinc chloride paste designated on the surface of the pack, FIGS. 1B and 1C represent different single-use dose specific, humectantly sealed container configurations, and FIG. 1D is a humectantly sealed unit dose package containing a pad or matrix impregnated with zinc chloride mixture for direct application to the skin;

DETAILED DESCRIPTION OF THE PREFERRED EMBODIMENTS

Figure 2A:
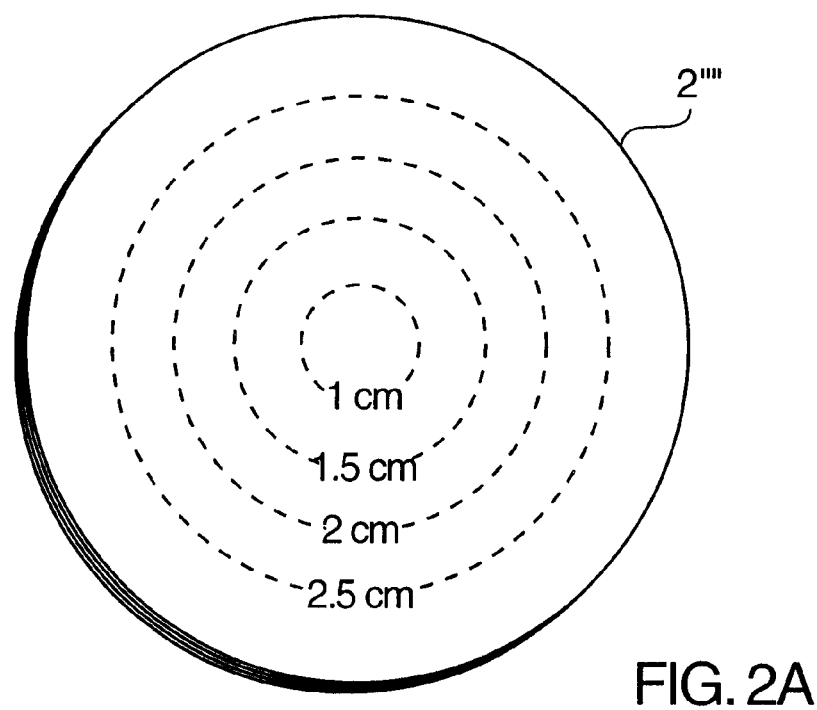
FIGS. 2A and 2B show another zinc chloride unit dosed package comprising a foil containing a matrix or pad impregnated with a dose specific quantity of zinc chloride mixture.

As shown in the accompanying drawings for purposes of illustration, the present invention is concerned with a zinc chloride mixture used in treating skin diseases, unit dosed packaging 2 (FIG. 1A), 2' (FIG. 1B), 2" (FIG. 1C), 2'" (FIG. 1D) and 2"" (FIGS. 2A and 2B), for the zinc chloride mixture, an applicator for the zinc chloride mixture, a kit 4 containing all the necessary components 6 needed to facilitate the use of zinc chloride in fixed tissue surgery, and a method of using the zinc chloride mixture to treat melanoma, skin cancer and other skin diseases.

The zinc chloride mixture of the present invention utilizing unit dosed packaging 2-2"" is shown in FIGS. 1–4. The use of a transdermal applicator containing the zinc chloride mixture is generally referred to in FIGS. 5–8 by the reference number 10, in FIG. 9 by the reference number 12, in FIG. 10 by the reference number 14 and in FIG. 11 by the reference number 16. For purposes of explanation, in each of the illustrated embodiments, functionally equivalent components will be given the same reference number.

In order to better understand the invention, the following background is given. The paste formulation developed by Dr. Mohs (34.5 mL zinc chloride saturated solution, 40 grams stibnite [80-mesh sieve], and 10 grams *sanguinaria canadensis*) has been the preferred form of fixative and has been used in humans since 1937. In this formulation zinc chloride is present 45% by weight, however, a wide range of concentrations may be acceptable from less than 0.1% to 60% or greater.

Sanguinaria is a chemically purified form of resin and plant alkaloids extracted from the rhizomes and roots of the Sanguinaria Canadensis plant (Bloodroot). The alkaloidal herb sanguinaria has long been known as an escharotic agent and treatment for skin cancer (Merck Index Seventh Edition, 1960, p 918). It contains the plant alkaloids sanguinarine, chelerythrine, protopine and homochelidonine. The cytotoxic alkaloids sanguinarine and chelerythrine, have been shown to uncouple oxidative phosphorylation and inhibit reverse transcriptase enzyme and to have anti-cancer activity (Usher, G. *A Dictionary of Plants Used by Man.* Hafner Press, 1974, p 219; Yance, D R, *Herbal Medicine. Healing & Cancer.* Keats; 1999, p 129). The sanguinaria also functions as a binder and thickening agent in the paste.

Stibnite is believed to act as a granular matrix. Alternative paste formulas used in the treatment of human skin cancer have retained the zinc chloride and Sanguinaria, but have substituted titanium dioxide, turmeric, and galangal for the inert stibnite.

The possibility of enhancing the zinc chloride fixative paste developed by Dr. Mohs with pharmacologically active additives has been investigated as a part of this invention. The additives studied were taxol, podophyllum resin, fluorouracil and urea. In the taxol (paclitaxel) mixture, paclitaxel, an extremely expensive, potent, and highly active plant alkaloid) is added at a 0.01% concentration (similar to other powerful dermatologic treatment preparations, e.g. Retin A creams and gels and many topical corticosteroids). However, a wide range of concentrations may be acceptable from 0.001% to 90% or greater, depending on the zinc chloride formulation employed.

Taxol (paclitaxel) is a natural plant alkaloid derived from the yew tree (*Taxus brevifolia, Taxus yannanensis*). It is a well known microtuble-stabilizing chemotherapeutic agent for the treatment of many cancers, including melanoma (Mohith, R S, Mackenzie, H. *Taxol and vinorelbine: a new active combination for disseminated malignant melanoma. Anti-Cancer Drugs.* 1996, Feb; 7(2):161–5; Photiou A, et al. *In vitro synergy of paclitaxel* (*Taxol*) *and vinorelbine* (*navelbine*) *against human melanoma cell lines.* 11: Eur J Cancer 1997 March; 33(3): 463–70; Bedikian A Y et al. *P:Phase II trial of docetaxel in patients with advanced cutaneous malignant melanoma previously untreated with chemotherapy.* J Clin Oncol December 1995: 13(12): 2895–9; *Proc. Amer. Assoc. Cancer Res.* 40, March, 1999]

Copyright 1999 by the American Association for Cancer Research. #3219 Induction of apoptosis in human melanoma cell lines by taxol and IL-6;). A taxoid derivative of paclitaxel, docetaxel, has been reported to be effective as a first-line chemotherapy for human melanoma. (Verweij J et al. *Phase II studies of docetaxel in the treatment of various solid tumors, EORTC Early Clinical Trials Group and the EORTC Soft Tissue and Bone Sarcoma Group.* Eur J Cancer 1995; 31A Suppl 4: S21–4).

Local skin reactions occurring inadvertently from extravasations of Taxol (paclitaxel), in far greater concentration and dosage than recommended in the zinc chloride paste preparation, during intravenous injection for the treatment of ovarian, breast and other cancers, have been reported as mild. These reactions have consisted of tenderness, erythema and skin discoloration, and swelling. (*Physician's Desk Reference.* Medical Economics Co. 2000; p. 886).

In low concentration, the plant alkaloid paclitaxel mixes completely and fully with the resin and plant alkaloids of the Sanguinaria component of the fixative paste. The paste consistency and viscosity remains unchanged.

The depth of penetration of zinc chloride into the skin from the paste can be precisely controlled depending primarily on the thickness and area over which the fixative is applied. For example, a 1.5 mm thick application over a 2.0 cm diameter area of skin results in a 6.4 mm deep penetration, augmented centrally. (Mohs F E, *Mohs Chemosurgery Microscopically Controlled Surgery for Skin Cancer.* Charles C. Thomas 1978; p 12.).

Paclitaxel zinc chloride paste concentrations of 0.01%, 0.1%, 1%, and 10% have been experimentally applied to pig skin in varying thicknesses from paper thin to 1 mm thick over surface areas varying from 4 mm to 1.5 cm in diameter to determine whether the addition of the paclitaxel affects the zinc chloride penetration. No difference in depth of penetration was observed for any of the concentrations, different surface areas, or thicknesses when compared to zinc chloride fixative paste without paclitaxel. The preservative property of zinc chloride is believed to maintain the activity of the plant alkaloids indefinitely.

As the plant alkaloids are nitrogenous organic compounds, three widely used pharmacologically active nitrogenous organic dermatologic compounds, podophyllin resin, fluorouracil, and urea were tested in a similar fashion to paclitaxel and found to be completely compatible and mix fully with the zinc chloride fixative paste. Podophyllin is a natural plant extract from the dried roots of either *Podophyllum peltatum* or *P. emodi*. It is an antimitotic agent used for many years in the treatment of human warts. (Fitzpatrick T B, et al. *Dermatology in General Medicine,* McGraw-Hill 1999, p. 2724.) Podophyllin is added at a 0.01% concentration, although a wide range of concentrations may be acceptable from 0.001% to 90% or greater, depending on the zinc chloride formulation employed.

Flurouracil is used in the topical treatment of actinic keratoses, squamous cell carcinoma in situ (Bowen's disease) and basal cell carcinoma. (Fitzpatrick T B, et al. *Dermatology in General Medicine,* McGraw-Hill 1999 p. 2768–2769.) In the fluorouracil mixture the fluorouracil is added at a 0.1% concentration. However, depending on the zinc chloride concentration in the mixture, the concentration of fluorouracil may vary from less than 0.01% to greater than 20%.

Urea is a widely used dermatologic keratolytic agent that dissolves the intercellular matrix thereby enhancing the absorption of the zinc chloride mixture into the skin through the dead keratin layer. (Fitzpatrick T B, et al. *Dermatology in General Medicine,* McGraw-Hill 1999, p. 2723.) Urea is added at a 0.01% concentration, but may vary from less than 0.01% to greater than 40%.

The zinc chloride mixture of the present invention may include immunological adjuvants and/or chemotherapeutic agents such as 5-fluorouracil, imiquimod, podophyllum, paclitaxel, BCNU, DTIC, Cisplatinum, Tamoxifen, Vinblastine, Bleomycin, Interferon, Interleukin 2, or Melanoma Vaccine. Alternative paste formulations may be employed utilizing xanthan gum, ethoxylated lanolin, or stearic acid, alkyl polyglycosides, turmeric, titanium dioxide, galangal, or equivalent substitutes. The zinc chloride medication mixture may be in a form other than paste including injectable solution, and administered as a single dose injection. Although several different formulations have been described, the essence of the invention regarding any biologically active external zinc chloride medication mixture, whether in paste, liquid, injectable solution, matrix, or other form, in a single use, dose specific applicator (described below) and/or other facilitated topical administration system is equivalent.

The inventor has developed a simplified dressing for holding zinc chloride paste in place on the skin. It consists of a thin, dry layer of cotton, applied over the zinc chloride paste and then fastened securely with an occlusive dressing tape. In accordance with the invention, a transdermal applicator may be substituted to secure the zinc chloride paste in place or alternately the dressing tape and the single use specific dosed package of zinc chloride paste may be combined into a single humectantly sealed transdermal applicator 10–16. The single use applicators 10–16 of zinc chloride mixture can be sized to provide the precise dosage necessary. They also facilitate the use of the zinc chloride treatment method and allow the treating physician to easily control the dosage of zinc chloride administered while maintaining the zinc chloride in an environmentally controlled atmosphere.

Referring to FIGS. 1A–1D, there are shown four zinc chloride unit dosed packages. FIG. 1A illustrates a blister pack 2 containing a specific dose of zinc chloride paste which is designated on the surface of the pack. FIGS. 1B and 1C show different single-use dose specific, humectantly sealed container configurations 2' and 2". FIG. 1D shows a humectantly sealed unit dose package 2''' containing a pad or matrix aid impregnated or embedded with zinc chloride mixture for direct application to the skin. The pad or matrix 8 may be removed from the surrounding container and applied directly to the skin.

Figure 2B:
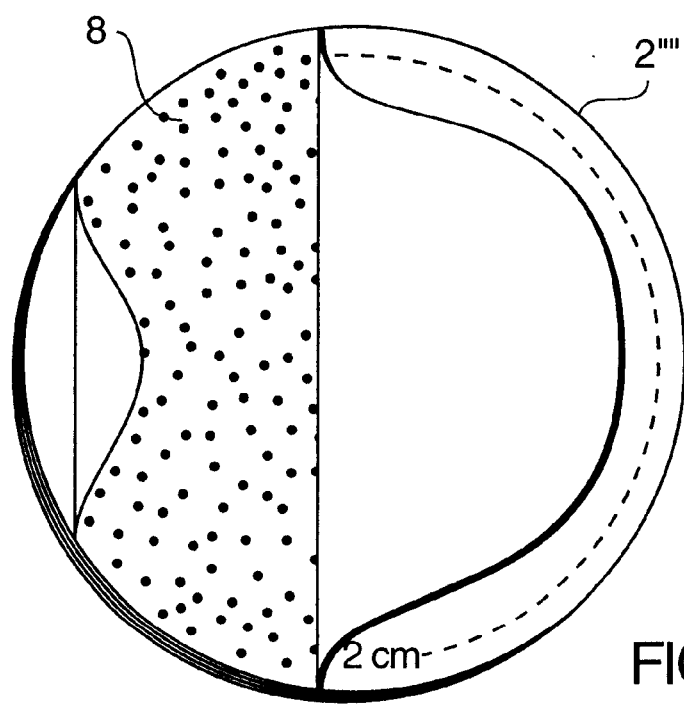

FIGS. 2A and 2B illustrate a unit dose package 2"" consisting of a foil or equivalent plastic material containing a matrix or pad 8 impregnated (embedded) with a dose specific quantity of zinc chloride mixture 22. The package is cut open with a pair of scissors. The pre-measured concentric rings serve as a cutting guide to facilitate precise surface area application. The matrix helps to secure the zinc chloride mixture into the treatment site. After the package has been cut to an appropriate size (as indicated by a selected concentric ring) the matrix or pad 8 is removed from the package for application onto the treatment site.

Figure 3:
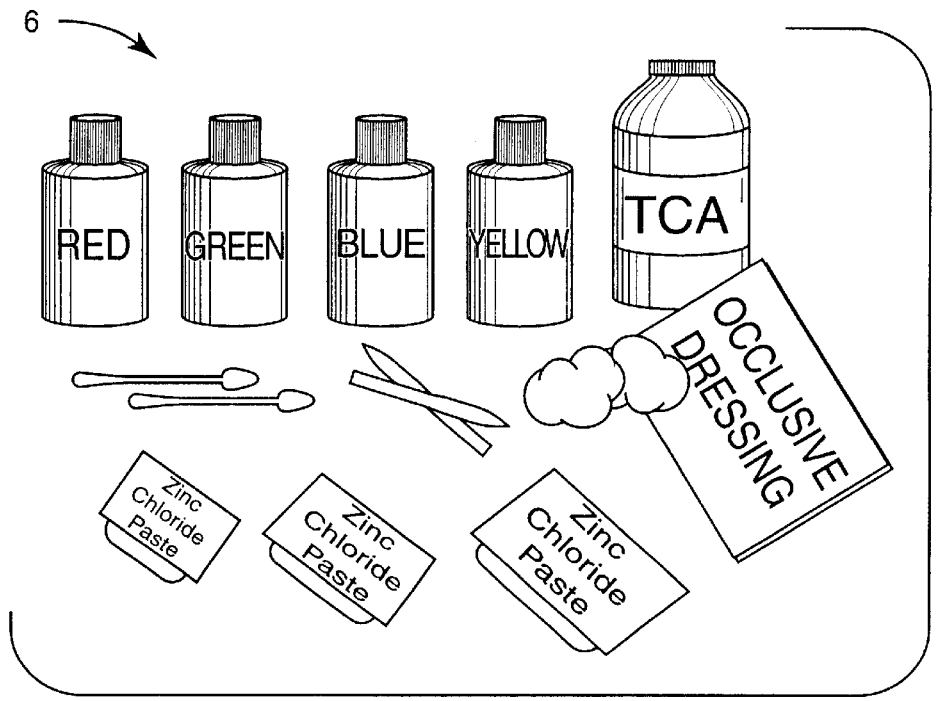
FIG. 3 represents the components of a zinc chloride treatment kit, including individually packaged dose specific zinc chloride paste blister pack containers, saturated solution trichloracetic acid solution used to dissolve dead keratin and help absorption of the zinc chloride, applicators, dry cotton balls used to hold the zinc chloride in place on the skin, occlusive dressing which is fastened over the cotton ball to securely hold it in place and provide an occlusive closure, and different colored dyes which may be used for color coding the edges of excised tissue specimens.
Figure 4:
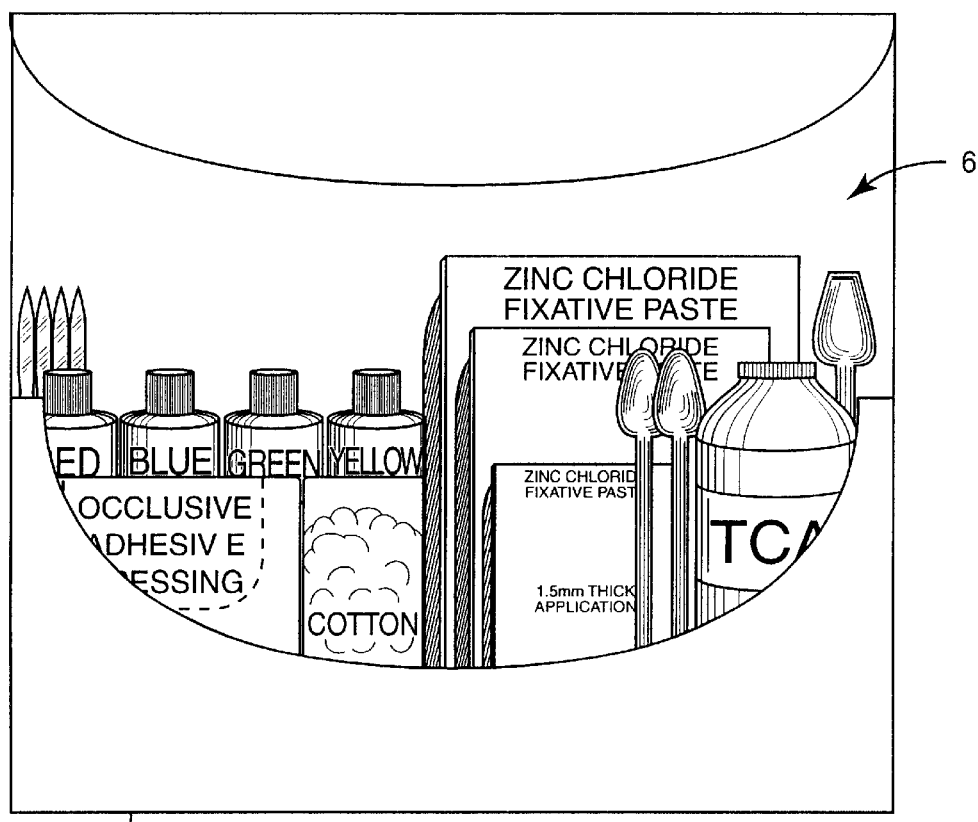
FIG. 4 is an elevational view of a treatment kit containing the items described in FIG. 3.
Figure 5:
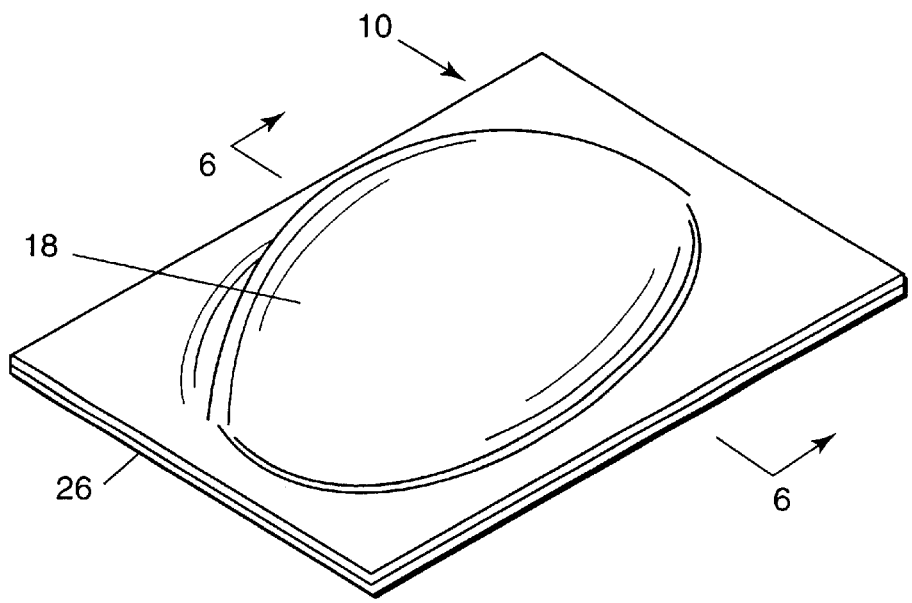
FIG. 5 is a top and side perspective view of a transdermal applicator embodying aspects of the present invention.
Figure 6:
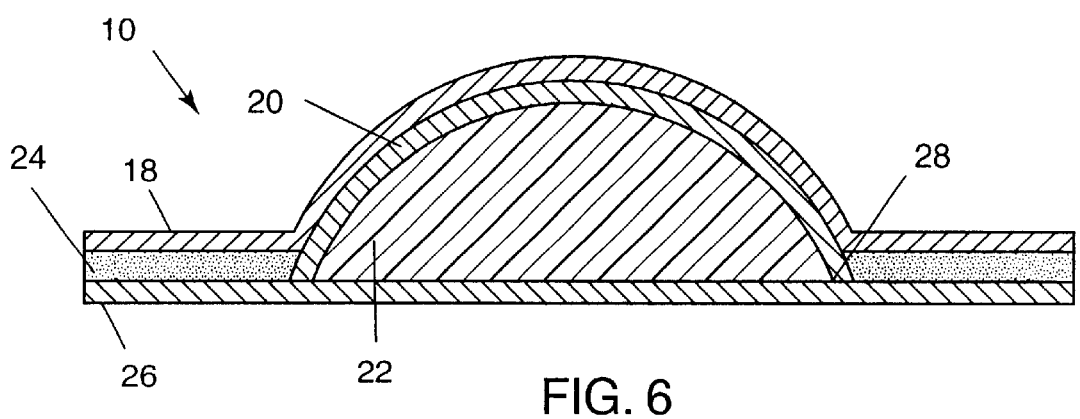
FIG. 6 is an enlarged cross-sectional view taken along the line 6—6 of FIG. 5.

FIG. 3 illustrates the components 6 of a zinc chloride chemosurgery treatment kit 4 (shown in FIG. 4). The components 6 include individually package dose specific zinc chloride paste blister pack containers 2, saturated solution trichloracetic acid solution used to dissolve dead keratin and help absorption of the zinc chloride, applicators, dry cotton balls used to hold the zinc chloride in place on the skin, occlusive dressing which is fastened over the cotton ball and provide an occlusive closure, and different colored dyes which may be used for color coating the edges of excised tissue specimens. Such components 6 may be easily packaged into the packaging 4 shown in FIG. 4. Additionally, the treatment kit may include items not illustrated: 1) surgical biopsy and excisional instruments; 2) hemostatic agents such as, e.g., zinc chloride, Gelfoam®, 30% aluminum chloride solution, absorbable suture; 3) postoperative dressings, Telfa pads, bandages, cleansing pads, mild keratolytic agents, and other items that facilitate chemosurgery.

The transdermal applicator 10 shown in FIGS. 5–8 comprises a reservoir system having a fluid impermeable backing 18, a secondary backing substrate 20 which is flexibly attached to the backing 18 to form a reservoir for the zinc chloride mixture 22, and an adhesive substrate 24 attached to the periphery of the backing 18. A fluid impermeable peel away strip 26 is attached to the adhesive substrate 24 to encapsulate the zinc chloride mixture 22 between the peel away strip 26 and the secondary backing 20 prior to use. The secondary backing substrate 20 forms a flange 30 which surrounds the periphery of the reservoir of zinc chloride 22 and is intended to hold the zinc chloride mixture 22 in place after application to the skin.

Figure 7:
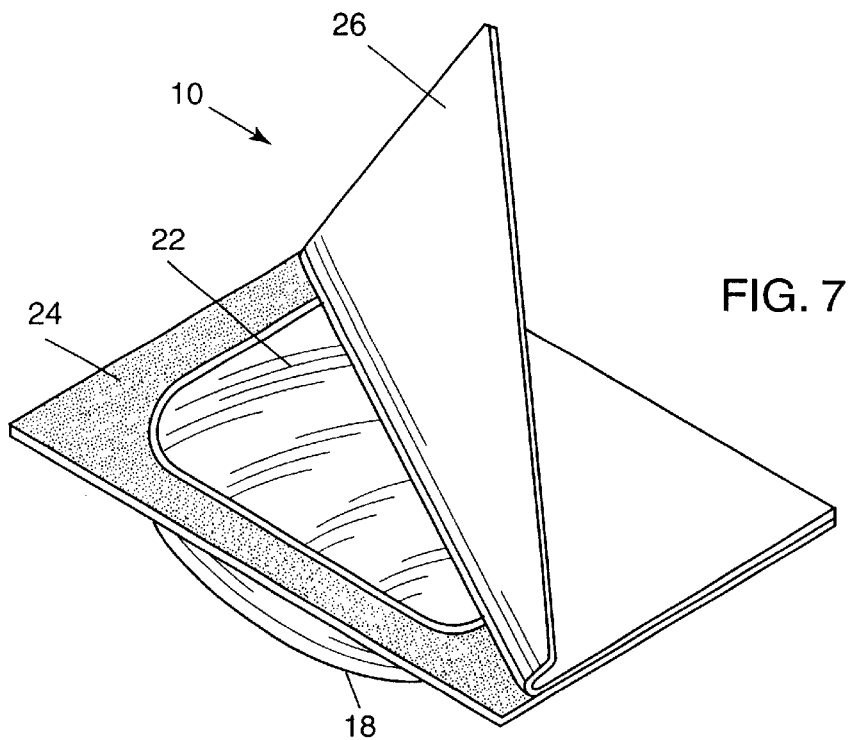
FIG. 7 is a bottom and side perspective view of the transdermal applicator of FIGS. 5 and 6, illustrating the removal of a peel away strip.
Figure 8:
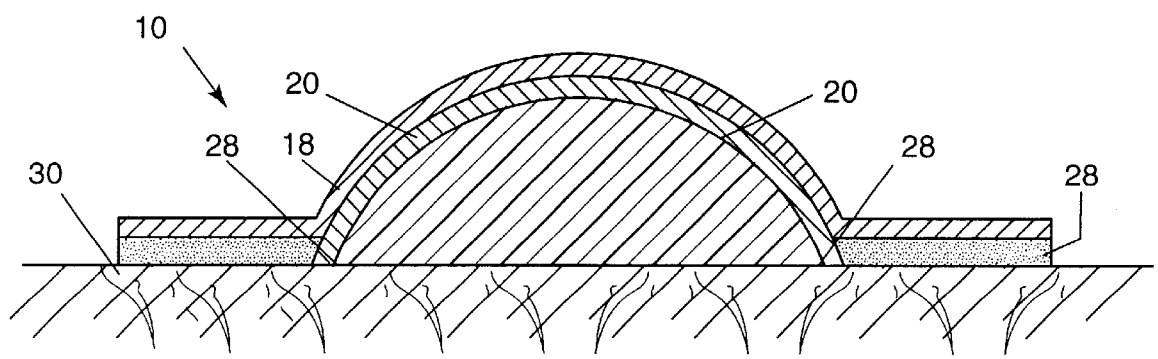
FIG. 8 is a cross-sectional view of the transdermal applicator, showing its use on an affected skin site.

The applicator 10 is administered by removing the peel away strip 26, as shown in FIG. 7, and applying the applicator 10 to the affected skin site 30, as shown in FIG. 8. The applicator 10 remains in place as the adhesive substrate layer 24 binds the applicator 10 to the skin.

Figure 9:
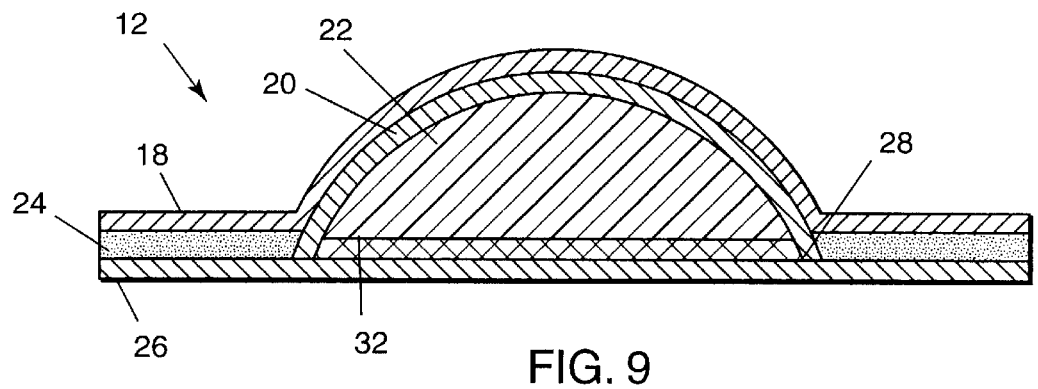
FIG. 9 is cross-sectional view similar to FIG. 6, illustrating a modified transdermal applicator having a drug rate controlling membrane between the peel away strip and a zinc chloride mixture in place.

Referring to FIG. 9, a second transdermal applicator 12 also includes the backing 18, the secondary backing substrate 20 flexibly attached to the backing 18, an adhesive substrate 24 attached to the periphery of the backing 18, and a peel away strip 26 attached to the adhesive substrate 24. In addition, the transdermal applicator 12 includes a drug rate controlling membrane 32 which acts to control the rate of absorption of the zinc chloride mixture 22 into the skin.

Figure 10:
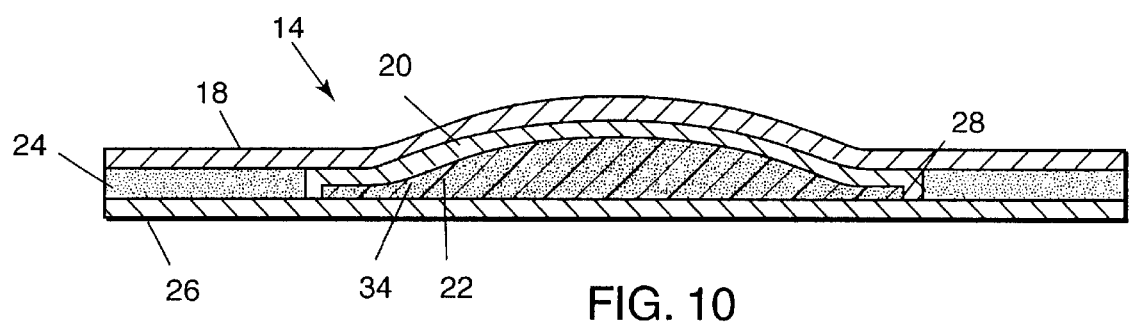
FIG. 10 is a cross-sectional view of another transdermal applicator, illustrating use of a drug matrix for holding the zinc chloride mixture.

Referring to FIG. 10, a third transdermal applicator 14 includes the backing 18, the secondary backing substrate 20 flexibly attached to the backing 18, an adhesive substrate 24 attached to the periphery of the backing 18, and a peel away strip 26 attached to the adhesive substrate 24. The transdermal applicator 14 also includes a polymer drug matrix 34 or equivalent matrix aid disposed between the backing 18 and the peel away strip 26. The matrix 34 stabilizes the paste zinc chloride mixture 22.

Figure 11:
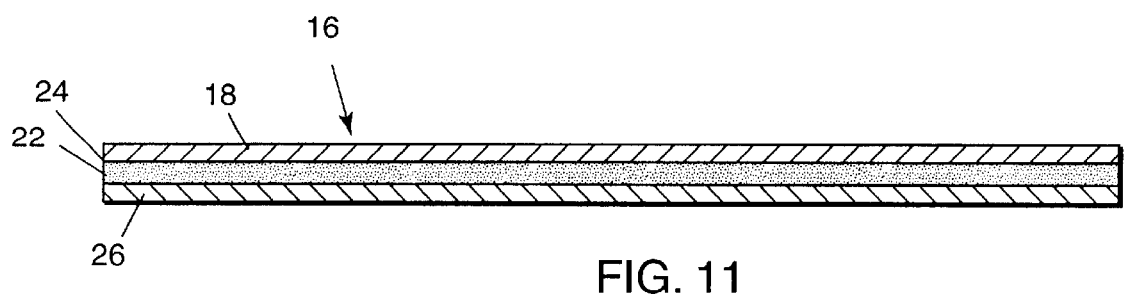
FIG. 11 is a cross-sectional view of yet another transdermal applicator having a single layer of zinc chloride impregnated adhesive disposed between a backing and the peel away strip.

FIG. 11 illustrates the most simple form of the transdermal applicator 16, wherein the applicator 16 has an adhesive substrate 24 impregnated with the zinc chloride mixture 22 and disposed between the impermeable backing 18 and the peel away strip 26.

The unit dose packages of zinc chloride paste shown in FIGS. 1A–1D and FIGS. 2A–2b, the complete zinc chloride treatment kit FIGS. 3 and 4, and/or the transdermal applicators 10–16 are beneficially used in treating melanoma, skin cancer and other skin diseases. After visually examining the affected site, and conducting a biopsy to confirm suspicion of cancer, the skin is typically treated before applying the zinc chloride mixture 22 with a keratolytic acid, preferably a saturated solution of trichloracetic acid. The keratolytic acid serves to dissolve the impermeable outer dead keratin layer of the skin allowing the zinc chloride mixture 22 to penetrate into the affected tissue. The zinc chloride mixture 22 and/or the transdermal applicators 10–16 may include skin penetration chemical enhancers (e.g. azelaic acids, nordihydroguauretic acid or other equivalent phenolic, carboxylic, organic, or plant derived acids, urea, sulphoxides, dimethyl sulfoxide, methyl sulfonylmethane, alcohols, polyols, alkanes, keratolytic acids, fatty acids, esters, amines, amides, terpenes, surfactants, cyclodextrins, and/or other solvents or keratolytic agents). The zinc chloride mixture 22 passes through the skin and into the abnormal growth area. The zinc chloride mixture 22 acts as a fixative by killing and histologically preserving the cells and tissue it comes into contact with.

The depth and area of tissue which is fixed can be precisely controlled by the surface area to be treated and the total quantity of zinc chloride mixture 22 applied. The depth of penetration of zinc chloride into the skin can vary from a fraction of a millimeter to more than a centimeter depending on both the thickness and diameter of the application (Mohs F E, *Mohs Chemosurery Microscopically Controlled Surgery for Skin Cancer.* Charles C. Thomas 1978; p. 12). Therefore, unit dose packages and applicators 10–16 can be manufactured which are of varying size and contain varying quantities of zinc chloride 22 so as to be dose specific. Other advantages of utilizing unit dose packaging and/or transdermal applicators 10–16 include the relative simple and inexpensive manufacturing process. Additionally unit dose packaging and the treatment kit illustrated in FIGS. 1–4 as well as the applicators 10–16 facilitate use by both the physician and the patient. Furthermore, the zinc chloride mixture 22 is humectantly sealed from the environment, preventing the paste form of the mixture 22 from undesirably hardening or liquefying.

Figure 12:
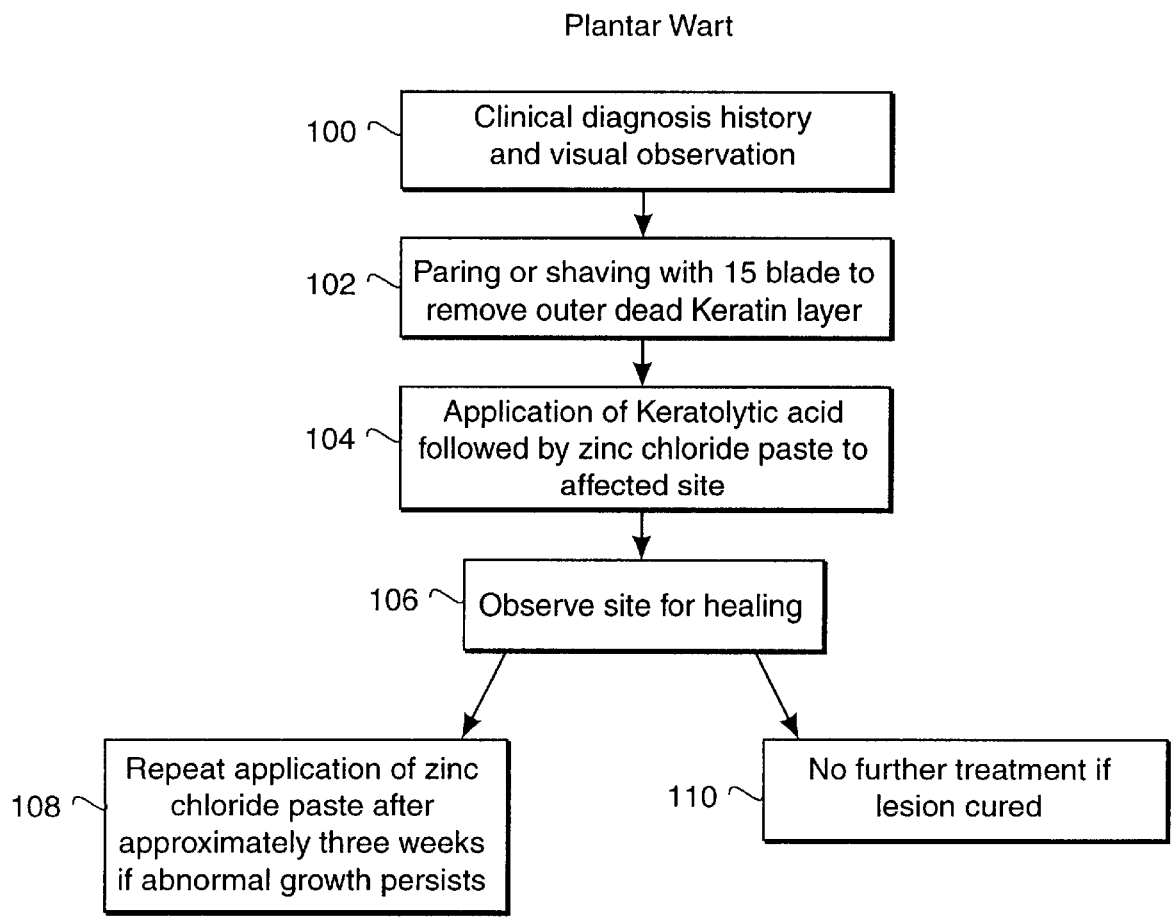
FIG. 12 is a flow chart illustrating the steps taken to remove a plantar wart in accordance with the present invention.

As illustrated in the flow chart of FIG. 12, plantar warts can be treated with the zinc chloride paste, utilizing unit dose packaging and treatment kit or a dose specific transdermal applicator 10–16. The patient's history is taken and a clinical diagnosis and visual observation of the wart is conducted (100). The outer dead keratin layer of the wart is then pared with preferably a 15 surgical blade to remove the outer dead keratin layer (102). A saturated solution of trichloracetic acid or equivalent keratolytic acid followed by application of zinc chloride paste is applied to the affected site (104). The site is later observed for healing (106) and the treatment is repeated in three weeks if wart persistence occurs (108). Once the lesion is cured, no further treatment is necessary (110).

Basal and squamous cell skin cancer is the most common of all human cancers and is increasing epidemically worldwide. Many of these skin cancers are best treated by sophisticated surgical techniques. However, there are many areas of the world, clinics and facilities, where such surgical treatment is too sophisticated and technically impossible to achieve.

Figure 13:
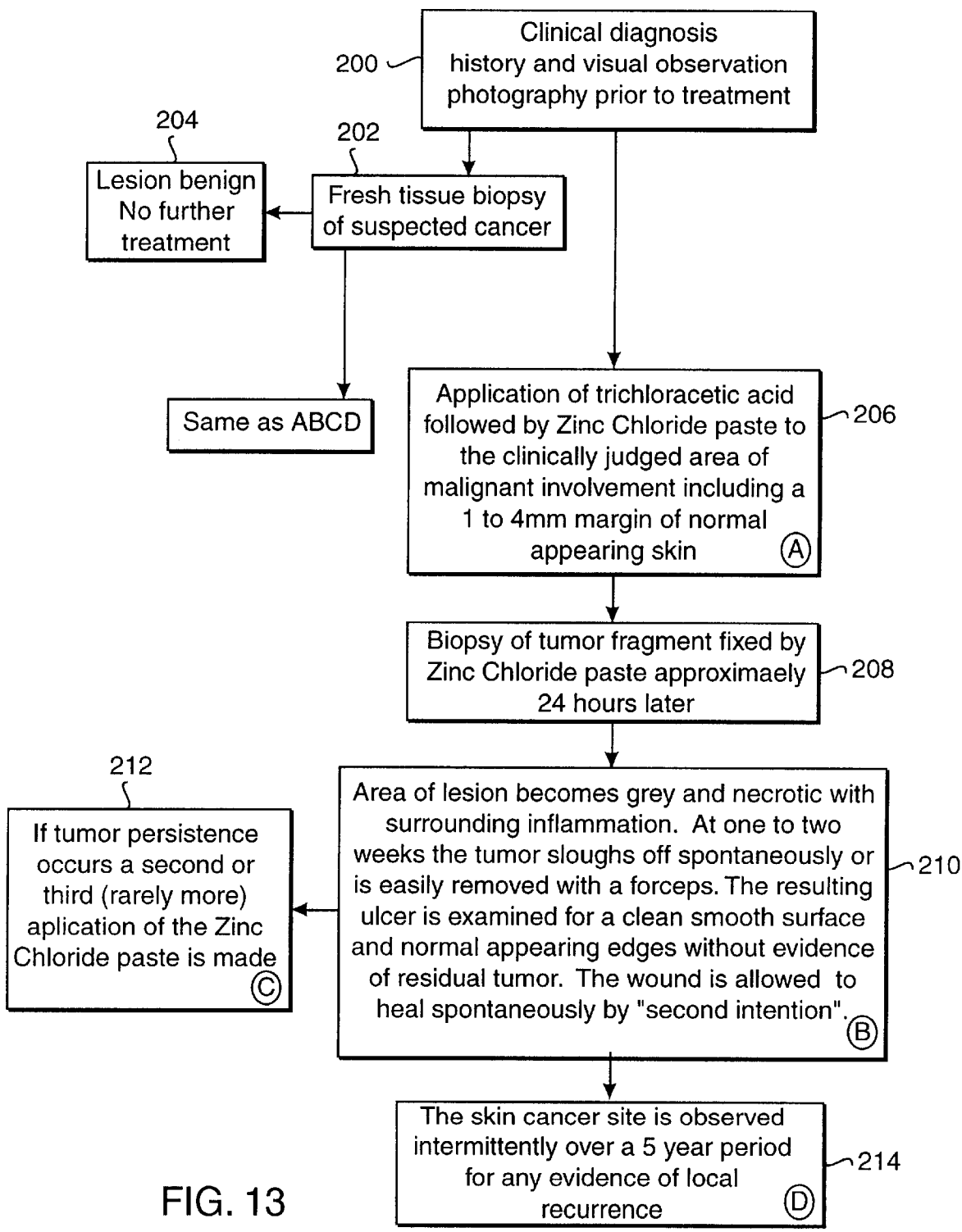
FIG. 13 is a flow chart illustrating the steps taken to remove basal or squamous skin cancer growths in accordance with the present invention.

A simplified technique for the treatment of these malignant skin tumors utilizing the zinc chloride mixture and applicators is illustrated in the flow chart of FIG. 13. Prior to treatment, a history is taken and photographs may be obtained (200). If cancer is suspected, tumors are preferably biopsied before treatment (202) and if the lesion is found to be benign, there is no further treatment (204). If the biopsy concludes cancerous tissue, a keratolytic acid, such as trichloracetic acid, is placed on the clinically judged site of malignant involvement and a one to four millimeter margin of normal skin, followed by an application of the zinc chloride mixture (206). Dead keratin may be pared from the surface of a heavily crusted tumor using a surgical blade prior to the application of the keratolytic acid.

The paste is permitted to act for 18 to 24 hours at which time maximum penetration occurs. Since zinc chloride paste preserves histology, the tumor fragment required for histologic examination can be removed with a scalpel or punch biopsy instrument the day after the application of the paste (208). The biopsy taken in the previously killed tissue can be performed without pain or hemorrhage. Local anesthesia and hemostasis are therefore, avoided.

The area of the lesion becomes gray and necrotic with surrounding inflammation and at one to two weeks the tumor sloughs off spontaneously or is easily removed with a forceps. A clean base of granulation tissue is achieved, which heals spontaneously by second intention with good or acceptable cosmetic results (210). If persistence occurs a second or third (rarely more) application of the zinc chloride mixture is made (212). The skin cancer site is observed intermittently over a five year period for any evidence of local recurrence (214).

Figure 14:
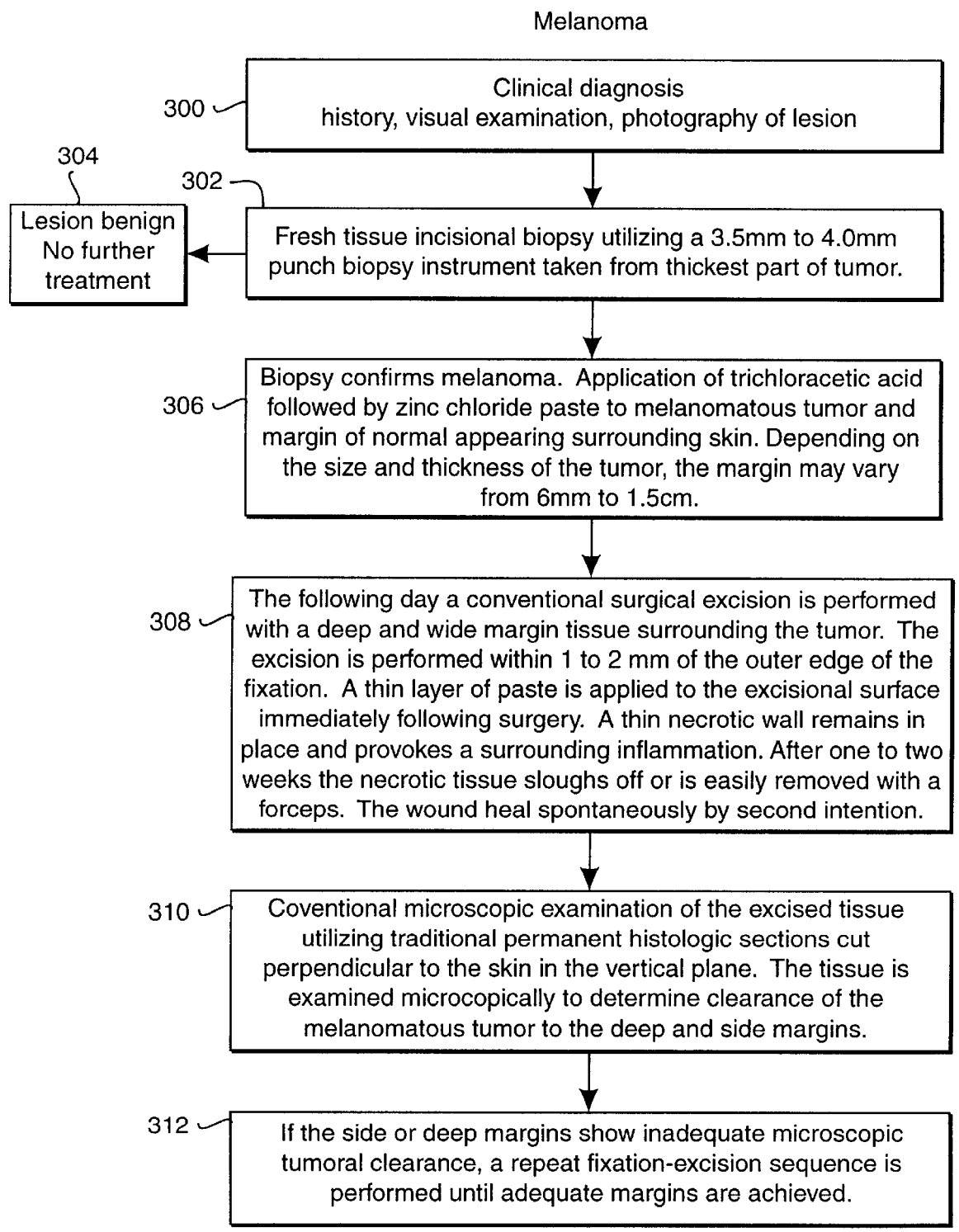
FIG. 14 is a flow chart illustrating the steps taken to remove melanoma skin cancer in accordance with the present invention.

Treatment of cutaneous melanoma, the most serious and potentially fatal form of skin cancer, is illustrated in the flow chart of FIG. 14. The site is diagnosed by visual inspection and photographs may be taken (300), followed by a fresh tissue (i.e. tissue not previously treated with zinc chloride fixative paste) incisional biopsy from the thickest part of the tumor utilizing a scalpel or 3–4 mm punch biopsy instrument (302). The biopsy is performed gently and the tissues are allowed to bleed outward. Hemostasis may be obtained by the application of 30% aluminum chloride or saturated solution of trichloracetic acid. If the lesion is found to be benign, no further treatment is taken (304).

However, if the diagnosis of melanoma has been confirmed, keratolytic acid (saturated solution trichloracetic acid) and zinc chloride paste mixture utilizing a dose specific container or applicator 10–16 are applied to the remaining tumor and a margin of surrounding normal appearing skin the day prior to surgery. The treated margin of normal appearing skin surrounding the visible melanoma can vary from 6 mm to 1.5 cm depending on the size and thickness of the tumor being treated (306). Surgery is performed 18 to 24 hours later in a conventional manner, removing a margin of tissue below and around the melanomatous tumor, with all incisions made through the previously killed tissue. The excision is performed within 1–2 mm of the outer edge of the fixation. A thin layer of zinc chloride paste mixture is applied to the excisional surface immediately following surgery. A thin wall of necrotic zinc chloride treated tissue is allowed to remain in place which provokes a strong inflammatory immune response enhancing host resistance against further or distant spread of the melanoma. After one to two weeks, the necrotic tissue sloughs off or is easily removed with a forceps. The wound heals spontaneously by second intention (308).

The excised specimen is examined microscopically in a conventional manner (traditional permanent histologic section cut vertically perpendicular to the skin) to determine clearance of the tumor to the deep and side margins. The edges of the excised specimen may be color coded by the application of dyes for precise orientation (310).

Unlike Mohs fixed tissue technique, which requires repetitive surgeries for treating a melanoma, the vast majority of melanomas can be successfully treated in a single session using this simplified method. However, on rare occasion microscopic examination may indicate the need for a deeper and/or wider surgery until adequate margins are achieved (312). Since all incisions are made through the tissue previously killed by zinc chloride a narrower margin of surrounding normal appearing skin than in conventional fresh tissue surgery can be safely removed without the risk of disrupting invisible satellite lesions. In a study of 200 melanoma patients subclinical microscopic extensions beyond the visible tumor were found to be 6 mm or less in 80% of the cases irregardless of the size or depth of invasion of the melanoma. The greatest extension was 1.5 cm from the visible margin. (Mikhail, G R, *Mohs Micrographic Surgery*. W. B. Saunders 1991; pp. 282–283). Bleeding may occur from larger arterioles feeding the affected site. Hemostasis may be secured by the application of 30% aluminum chloride, saturated solution trichloracetic acid, or Gelfoam. Absorbable suture ligatures may be necessary for larger vessels. Electrocoagulation is avoided.

Although fixed tissue zinc chloride treatment has been described somewhat in detail with respect to plantar wart, basal and squamous cell carcinomas and melanomas, "chemosurgery" has also been reported to be effective in the treatment of the following tumors: neoplasms and carcinomas of the parotid gland, bone, larynx, mouth, accessory nasal sinuses, lips, breast and anal region, sarcomas, actnic and seborrheic keratoses, keratoacanthoma, hemangiomas, lymphangiomas, nevi, warts and other miscellaneous epithelial growths (Mohs F E. *Chemosurgery Microscopically Controlled Surgery for Skin Cancer*. Charles C. Thomas, 1978). An advantage of using the zinc chloride treatment is that skin cancer patients who are infected with the AIDS virus can be safely treated using zinc chloride paste. HIV is inactivated by zinc chloride, thus minimizing the danger of infection to surgical or laboratory personnel.

Zinc chloride paste has beneficial effects in a variety of other skin diseases because it has a bactericidal effect on infected tissues and also stimulates the angiogenesis of granulation tissue which results in rapid spontaneous wound healing. For example, zinc chloride paste is beneficial in the healing of the infected, necrotic tissue of diabetic gangrene. Following superficial wound debridement a small dose of paste is applied to the affected site from a dose specific container. The treatment may be repeated in two to three weeks. The wound is sterilized and granulation tissue is stimulated by the zinc chloride paste. It has been reported among diabetics that 75% of appendages are saved through treatment with zinc chloride paste rather than with limb amputation. (Mikhail G R. *Mohs Micrographic Surgery*. W. B. Saunders, 1991; p 47). Due to the potential for severe complications in diabetic gangrene, a multidisciplinary medical and vascular surgical approach is recommended. Tetanus, chronic osteomyelitis, tuberculous ulcers and other chronic skin infections, arteriosclerotic gangrene, and frostbite and thermal gangrene have also been benefited with the application of zinc chloride paste.

Although several embodiments have been described in detail for purposes of illustration, various modifications may be made to each without departing from the scope and spirit of the invention. Accordingly, the invention is not to be limited, except as by the appended claims.

What is claimed is:

1. A unit dose packaging for treating skin cancer, moles, warts, keratoses, skin tumors and melanoma, consisting of:
   a backing;
   a zinc chloride mixture consisting of zinc chloride, an alkaloidal herb, and an inert matrix, wherein the zinc chloride mixture is disposed within the inert matrix, and comprises 45% concentration of zinc chloride by weight, an 11% concentration by weight of the alkaloidal herb *Sanguinaria canadensis*, and at least a 0.001% concentration by weight of the alkaloidal herb taxoid, taxol, paclitaxel, or a derivative thereof;

a matrix substrate attached to the backing and embedded with the zinc chloride mixture; and a peel away strip for encapsulating the zinc chloride mixture between the backing and the peel away strip.

2. The unit dose packaging of claim 1, wherein the zinc chloride mixture includes a skin penetrating enhancing agent to facilitate the absorption or the zinc chloride mixture into the skin.

3. The unit dose packaging of claim 1, wherein the alkaloidal herb consists of a taxoid, taxol, paclitaxel alkaloid or a derivative thereof.

4. The unit dose packaging of claim 3, wherein the concentration of the alkaloidal herb is less than 10% by weight.

5. The unit dose packaging of claim 3, wherein the concentration of the alkaloidal herb is at least 0.001% by weight.

6. The unit dose packaging of claim 1, wherein the inert matrix is granular and is impregnated with the medicinal zinc chloride mixture.

7. The unit dose packaging of claim 1, wherein the medicinal zinc chloride mixture is disposed within an inert matrix which is attached to a backing to form a medicated disc.

8. The unit dose packaging of claim 7, wherein the disk is capable of being cut to a preferred size.

9. The unit dose packaging of claim 1, wherein the backing and peel away strip are fluid impermeable.

10. The unit dose packaging of claim 1, wherein the unit dose packaging is capable of being cut to a preferred size.

11. The unit dose packaging of claim 1, wherein the matrix substrate consists of cotton, paper, fabric, plastic, natural fiber, or synthetic fiber which is attached to the backing.

12. The unit dose packaging of claim 1, wherein the matrix substrate consists of a gum which is attached to the backing.

13. The unit dose packaging of claim 1, wherein the matrix substrate consists of a resin which is attached to the backing.

14. The unit dose packaging of claim 1, wherein the matrix substrate consists of a rubber-based vehicle which is attached to the backing.

15. A unit dose packaging for treating skin cancer, moles, warts, keratoses, skin tumors and melanoma, consisting of:
    a backing;
    a zinc chloride mixture including an alkaloidal herb *Sanguinaria canadensis* disposed adjacent to the backing;
    a matrix substrate embedded with the zinc chloride mixture;
    an adhesive substrate fixed to the backing for securely positioning the zinc chloride mixture over a skin abnormality; and
    a peel away strip for encapsulating the zinc chloride mixture between the backing and the peel away strip.

16. A unit dose packaging for treating skin cancer, moles, warts, keratoses, skin tumors and melanoma, consisting of:
    a backing;
    a zinc chloride mixture including an alkaloidal herb *Sanguinana canadensis* disposed adjacent to the backing;
    a matrix substrate embedded with the zinc chloride mixture;
    a peripheral flange having an adhesive substrate for securely positioning the zinc chloride mixture over a skin abnormality, and fastening the unit dose packaging to the surrounding skin; and
    a peel away strip.

17. A unit dose packaging of a medicinal zinc chloride mixture for treating skin cancer, moles, warts, keratoses, skin tumors and melanoma, including a treatment kit consisting of a fluid impermeable, humectantly sealed and packaged, dose specific zinc chloride mixture containers/applicators of varying sizes and concentrations consisting of a backing, the zinc chloride mixture including an alkaloidal herb *Sanguinaria canadensis* disposed adjacent to the backing, a matrix substrate embedded with the zinc chloride mixture, and a peel away strip for encapsulating the zinc chloride mixture between the backing and the peel away strip, instructional material, keratolytic acid including saturated solution bi-trichloracetic acid, skin penetration enhancing agents, hemostatic agents, adhesive dressing tape, cotton applicators, suture material, surgical instruments including surgical biopsy and punch biopsy instruments, curettes, hemostats, scissors, surgical blades and blade holders, needle holders, forceps, surgical file.

18. A unit does packaging for treating skin cancer, moles, warts, keratoses, skin tumors and melanoma, consisting of:
    a backing;
    a zinc chloride mixture consisting of zinc chloride, an alkaloidal herb, and an inert matrix, wherein the zinc chloride mixture is disposed within the inert matrix, and comprises 45% concentration of zinc chloride by weight, an 11% concentration by weight of the alkaloidal herb *Sanguinaria canaclensis*, and at least a 0.001% concentration by weight of the alkaloidal herb taxoid, taxol, paclitaxel, or a derivative thereof, wherein the zinc chloride mixture is disposed adjacent to the backing; and
    a peel away strip for encapsulating the zinc chloride mixture between the backing and the peel away strip.

19. The unit dose packaging of claim 6, wherein the granular inert matrix comprises stibnite.

20. The unit does packaging of claim 17, wherein the zinc chloride mixture includes the alkaloidal herb taxoid, taxol, paclitaxel or a derivative thereof.

21. The unit dose packaging of claim 17, wherein the matrix substrate consists of gelatin.

* * * * *